United States Patent [19]

Haag et al.

[11] Patent Number: 5,304,695
[45] Date of Patent: Apr. 19, 1994

[54] DOUBLE BOND ISOMERIZATION OF OLEFIN-CONTAINING FEEDS WITH MINIMAL OLIGOMERIZATION USING PERMANENTLY SURFACE ACIDITY DEACTIVATED ZEOLITE CATALYSTS

[75] Inventors: Werner O. Haag, Lawrenceville, N.J.; Jose G. Santiesteban, Yardley, Pa.

[73] Assignee: Mobil Oil Corporation, Fairfax, Va.

[21] Appl. No.: 20,947

[22] Filed: Feb. 22, 1993

[51] Int. Cl.⁵ .............................................. C07C 5/25
[52] U.S. Cl. .................................... 585/666; 585/664
[58] Field of Search .................. 585/666, 664; 502/85

[56] References Cited

U.S. PATENT DOCUMENTS

| | | | |
|---|---|---|---|
| 2,804,490 | 8/1957 | Belden | 260/683.4 |
| 3,442,795 | 5/1989 | Trenton et al. | 208/120 |
| 3,800,003 | 3/1974 | Sobel | 260/683.49 |
| 3,864,424 | 2/1975 | Brennan et al. | 585/664 |
| 4,101,595 | 7/1978 | Chen et al. | 260/668 |
| 4,388,177 | 6/1983 | Bowes et al. | 208/111 |
| 4,418,235 | 11/1983 | Haag et al. | 585/474 |
| 4,419,220 | 12/1983 | LaPierre et al. | 208/111 |
| 4,520,221 | 5/1985 | Chen | 585/517 |
| 4,568,786 | 2/1986 | Chen et al. | 585/517 |
| 4,605,787 | 8/1986 | Chu et al. | 568/697 |
| 4,749,819 | 6/1988 | Hamilton, Jr. | 585/329 |
| 4,788,375 | 11/1988 | Garwood et al. | 585/533 |
| 4,870,038 | 9/1989 | Page et al. | 502/62 |
| 4,918,255 | 4/1990 | Chou et al. | 585/331 |
| 5,007,997 | 4/1991 | Zones et al. | 585/666 |
| 5,015,361 | 5/1991 | Anthes et al. | 208/111 |
| 5,177,281 | 1/1993 | Haag et al. | 585/324 |
| 5,237,120 | 8/1993 | Haag et al. | 585/666 |

FOREIGN PATENT DOCUMENTS

| | | | |
|---|---|---|---|
| 0247802 | 6/1990 | European Pat. Off. | 585/666 |
| 0259526 | 9/1991 | European Pat. Off. | 502/64 |

Primary Examiner—Anthony McFarlane
Attorney, Agent, or Firm—Alexander J. McKillop; Dennis P. Santini; Laurence P. Hobbes

[57] ABSTRACT

A method is disclosed for the double bond isomerization of alpha olefin-containing feeds, e.g., conversion of 1-butene-containing hydrocarbon streams to 2-butene-rich product streams, wherein oligomer by-products are minimized. The process uses a catalyst composition comprising a zeolite whose surface has been at least partially deactivated for acid catalyzed reactions by treatment with an aluminum chelating agent, e.g., oxalic acid, which possesses an average cross section diameter greater than that of the zeolite pores.

20 Claims, No Drawings

DOUBLE BOND ISOMERIZATION OF OLEFIN-CONTAINING FEEDS WITH MINIMAL OLIGOMERIZATION USING PERMANENTLY SURFACE ACIDITY DEACTIVATED ZEOLITE CATALYSTS

FIELD OF THE INVENTION

This invention relates to a highly selective method for the double bond isomerization of alpha olefin-containing feeds, e.g., conversion of 1-butene-containing hydrocarbon streams to 2-butene-rich product streams. The process uses a catalyst composition comprising a zeolite whose surface has been at least partially permanently deactivated for acid catalyzed reactions by treatment with a surface-deactivating chelating agent which possesses an average cross section diameter greater than that of the zeolite pores, and which is capable of forming a chelate-Al complex.

BACKGROUND OF THE INVENTION

The demand for internal double-bond olefins has recently increased. For example, 2-butene-rich feeds have been found to be useful in the production of alkylate prepared by alkylation of isoparaffins with light olefins. The desirability of using butene-2 as compared to butene-1 as feedstock to an alkylation zone to produce high octane gasoline blending stocks is disclosed in U.S. Pat. No. 2,804,490. U.S. Pat. No. 3,800,003 presents a process in which a feed stream comprising butene isomers is passed into an isomerization zone to increase the quantity of butene-2 available for passage into a downstream alkylation zone. U.S. Pat. No. 4,918,255 discloses an alkylation process using a heterogeneous isoparaffin/olefin alkylation catalyst, e.g. $BF_3/Al_2O_3$, wherein the olefin feed is isomerized to reduce alpha olefin content using as isomerization catalyst alumina, silica, zirconia, chromium oxide, boron oxide, thoria, magnesia, aluminum sulfate or combinations thereof, as well as boron halide-modified metal oxide.

Double bond isomerization of olefins such as butene in the presence of catalysts of the pentasil type such as ZSM-5 and ZSM-11 at temperatures of 100° to 500° C. is disclosed in European Patent Application 0 129 899 to Hoelderich.

European Patent Application 0 247 802 to Barri et al. discloses restructuring olefins using tectometallosilicates of the Theta-1 type (ZSM-22) as well as ZSM-23 at relatively high reaction temperatures of 200° to 550° C. Table 4 thereof shows 1-butene to 2-butene selectivity (mol/mol) of Theta-1 catalyst in the conversion of 1-butene of 92.1% at 234° C. at 100 MPa pressure using an 11.5±2.8% vol/vol 1-butene in nitrogen feed.

U.S. Pat. No. 4,749,819 to Hamilton, Jr. exemplifies double bond isomerization of an alpha olefin feed (preferably $C_{12}$ to $C_{18}$) to produce a product having interior double bond isomerization using a ferrierite catalyst. The reference further teaches at column 5, lines 15 to 19, that "[o]ther aluminosilicates may be exemplified by ZSM-12, ZSM-22, ZSM-23 and ZSM-48."

It is not unexpected that a wide variety of catalysts can be used to isomerize 1-butene at high initial activity inasmuch as the double bond shift is one of the most facile among the hydrocarbon reactions. The thermodynamics of the reaction indicate that enhanced selectivity for 2-butenes occurs at lower temperatures and that relatively great selectivities are possible with a wide variety of catalysts at such temperatures. However, those catalysts which exhibit the desirable activity and stability for the double bond shift reaction can often produce unwanted oligomer by-products.

Accordingly, it would be desirable to provide a method for isomerizing alpha-olefins (or terminal double bond olefins) to internal double bond olefins, e.g., 1-butene feeds to 2-butene rich products, over a catalyst which exhibits high 1-butene conversion and 2-butene selectivity, while minimizing oligomer by-product formation.

It is known in the art that surface acidity of zeolitic catalysts can be modified by treatment with various base reagents. U.S. Pat. No. 4,870,038 to Page et al discloses a process for producing substantially linear hydrocarbons by oligomerizing a lower olefin at elevated temperature and pressure with siliceous acidic ZSM-23 whose surface is rendered substantially inactive for acidic reactions, e.g., by contact with 2,4,6-collidine (2,4,6-trimethylpyridine, gamma-collidine). U.S. Pat. No. 5,015,361 to Anthes et al discloses a method for catalytic dewaxing which employs zeolite catalysts surface acidity deactivated with bulky amines. The reduction in surface acidity serves to reduce the amount of lower value cracked products obtained during dewaxing. U.S. Pat. No. 4,101,595 teaches the modification of zeolites by exchange and similar technology with large cations such as $N^+$ and $P^+$ and large branched compounds such as polyamines and the like. As disclosed in U.S. Pat. Nos. 4,520,221 and 4,568,786, zeolites which have been surface-deactivated by treatment with bulky dialkylamines are useful as catalysts for the oligomerization of lower olefins such as propylene to provide lubricating oil stocks.

Base treatments, however are often temporary in nature and require the continual provision of base in the feedstream in order to maintain the desired deactivation of the catalyst surface. Moreover, the bulky base can obstruct pores resulting in reduced intrapore activity of the zeolite and requiring higher temperatures, which are undesirable for internal double bond selectivity, and/or reduced space velocity.

Another approach to selectively deactivating the surface of zeolites involves dealumination of zeolite surfaces. Techniques for zeolite dealumination include hydrothermal treatment, mineral acid treatment with HCl, $HNO_3$, and $H_2SO_4$, and chemical treatment with $SiCl_4$ or ethylenediaminetetraacetic acid (EDTA). The treatments are limited, in many cases, in the extent of dealumination by the onset of crystal degradation and loss of sorption capacity. U.S. Pat. No. 4,419,220 to LaPierre et al discloses that dealumination of zeolite Beta via treatment with HCl solutions is limited to $SiO_2/Al_2O_3$ ratios of about 200 to 300 beyond which significant losses to zeolite crystallinity are observed.

U.S. Pat. No. 3,442,795 to Kerr et al. describes a process for preparing highly siliceous zeolite-type materials from crystalline aluminosilicates by means of a solvolysis, e.g. hydrolysis, followed by a chelation. In this process, the acid form of a zeolite is subjected to hydrolysis, to remove aluminum from the aluminosilicate. The aluminum can then be physically separated from the aluminosilicate by the use of complexing or chelating agents such as ethylenediaminetetraacetic acid or carboxylic acid, to form aluminum complexes that are readily removable from the aluminosilicate. The examples are directed to the use of EDTA to remove alumina.

EP 0 259 526 B1 discloses the use of dealumination in producing zeolite ECR-17. The preferred dealumination method involves a combination of steam treatment and acid leaching, or chemical treatments with silicon halides. The acid used is preferably a mineral acid, such as HCl, HNO$_3$ or H$_2$SO$_4$, but may also be weaker acids such as formic, acetic, oxalic, tartaric acids and the like.

U.S. Pat. No. 4,388,177 to Bowes et al. discloses the preparation of a natural ferrierite hydrocracking catalyst by treatment with oxalic acid to impart catalytic activity for converting slightly branched as well as straight chain hydrocarbons in hydrodewaxing and naphtha upgrading. Increased activity is believed to arise from removal of iron, sodium and other impurities by such treatment.

As far as is known, surface-dealuminated zeolites have heretofore not been used as double-bond isomerization catalysts.

SUMMARY OF THE INVENTION

The present invention relates to a method for isomerizing a terminal double bond olefin-containing organic feedstock to a product enriched in internal double bond olefin which comprises contacting said feedstock under double bond isomerization conditions, with a double bond isomerization catalyst comprising a zeolite containing surface aluminum whose surface has been at least partially deactivated for acid catalyzed reactions by treatment with a surface-dealuminating chelating agent capable of forming a chelate-Al complex which possesses an average cross section diameter greater than that of the zeolite pores. The use of such deactivated catalyst results in reduced oligomerization by-products in the double bond isomerization product stream and permits the use of higher space velocities than with comparable base deactivated catalysts.

This invention also relates to a highly selective method for the double bond isomerization of alpha olefin-containing feeds, e.g., conversion of 1-butene-containing hydrocarbon streams to 2-butene-rich product streams. The process uses a catalyst composition comprising a zeolite whose surface has been at least partially permanently deactivated for acid catalyzed reactions by treatment with a surface-deactivating chelating agent which possesses an average cross section diameter greater than that of the zeolite pores, and which is capable of forming a chelate-Al complex.

The internal double bond olefin-rich, e.g. 2-butene, stream resulting from the isomerization method of the present invention can be utilized as the olefin stream in isoparaffin-light olefin alkylation. The alkylate made therefrom is an especially valuable component of the gasoline pool as it possesses both high research and motor octane numbers.

The use of a zeolite double bond isomerization catalyst which has been at least partially surface-deactivated in accordance with the invention possesses a decided advantage over the same zeolites the acid sites of which remain substantially intact. In the case of the latter, the acid catalyst activity which is exhibited at the zeolite surface is responsible for an undesirable incidence of oligomerization of olefins, especially iso-olefin, e.g. isobutylene, which decreases the amount of desired internal double bond olefin product resulting from the double bond isomerization operation in which such zeolites are used. In contrast to such unmodified zeolites, the process herein employs a zeolite whose surface acid catalyst activity, and therefore olefin oligomerization activity, has been significantly reduced by treatment with a surface-deactivating agent which dealuminates the catalyst surface. Such catalysts also permit the double bond isomerization reaction to take place in the liquid phase while minimizing oligomer make which occurs under the higher pressures associated with liquid phase operation. Finally, such catalysts maintain high activity for an extended period under conditions of low temperature and high pressure. The result, then, in the case of the double bond isomerization process of the present invention is a higher yield of desired internal double-bond olefins and a reduced yield of undesired oligomerized olefin products.

DETAILED DESCRIPTION OF THE INVENTION

The present invention relates to a method for isomerizing a 1-olefin-containing organic feedstock to convert a substantial portion of said 1-olefin, e.g., 1-butene, to 2-olefin, e.g., 2-butene, by contacting the feedstock under double bond isomerization conditions. The isomerizing method of the present invention can be carried out at temperatures of less than 200° C., for example, 20 to 150 C, preferably 50 to 130 C, weight hourly space velocities of said feedstock based on total feed between 0.5 and 100 hr$^{-1}$, preferably between 1 and 80 hr$^{-1}$; ; total pressure between 100 and 10000 kPa, preferably between 300 and 6000 kPa. The process can be carried out so as to yield at least 85 wt % 2-olefin, preferably at least 88 wt % 2-olefin, in the olefinic product, and less than 15 wt %, preferably less than 12 wt % oligomeric product. The catalyst employed under the conditions of the present invention can have a catalyst stability parameter (CSP) of greater than 375, preferably greater than 800.

The CSP describes the useful cycle life of the catalyst, expressed in kg feed processed per kg catalyst. The useful cycle life is reached when the composition of the olefinic product drops to less than 85% 2-olefins. The catalyst can then be regenerated by conventional means, such as hydrogen regeneration or oxidative combustion of carbonaceous deposits. The catalysts used in the present invention are especially suited to such regeneration in that they generally require no further treatment after regeneration to reduce surface acidity, in contrast to base-selectivated catalysts which do.

Although the present method can be carried out with the feed in the gaseous state, it is preferably carried out in the liquid phase in order to avoid costly and uneconomical vaporization and condensation steps. In order to assure liquid phase operation and to keep the pressure at acceptably low limits, the temperature is preferably kept below the critical temperature of the butenes, which is about 146° C.

The 2-olefin rich stream resulting from the isomerization method of the present invention can be utilized as the olefin stream in isoparaffin-light olefin alkylation. The alkylate made therefrom is an especially valuable component of the gasoline pool as it possesses both high research and motor octane numbers, More particularly, the present invention may be incorporated into a continuous integrated process for producing alkylate from isoparaffin and olefins wherein the present method of isomerization provides a product used as an olefins source for alkylation. The alkylate thus prepared exhibits high quality based on both research and motor octane numbers and as such is particularly well suited for blending into the gasoline pool.

Catalyst

The preferred catalysts, exemplified by ZSM-22, ZSM-23, and ZSM-35, are members of a unique class of zeolites. They have channels described by 10-membered rings of T (=Si or Al) or oxygen atoms, i.e., they are intermediate pore zeolites, distinct from small pore 8-ring or large pore 12-ring zeolites. They differ, however, from other intermediate pore 10-ring zeolites, such as ZSM-5, ZSM-11, ZSM-57 or stilbite, in having a smaller 10-ring channel. If the crystal structure (and hence pore system) is known, a convenient measure of the channel cross-section is given by the product of the dimensions (in angstrom units) of the two major axes of the pores. These dimensions are listed in the "Atlas of Zeolite Structure Types" by W. M. Meier and D. H. Olson, Butterworths, publisher, Second Edition, 1987. The values of this product, termed the Pore Size Index, are listed in Table A.

TABLE A

| | | Pore Size Index | | |
|---|---|---|---|---|
| Type | Largest Ring Size | Zeolite | Axes of Largest Channel, A | Pore Size Index |
| 1 | 8 | Chabazite | 3.8 × 3.8 | 14.4 |
| | | Erionite | 3.6 × 5.1 | 18.4 |
| | | Linde A | 4.1 × 4.1 | 16.8 |
| 2 | 10 | ZSM-22 | 4.4 × 5.5 | 24.2 |
| | | ZSM-23 | 4.5 × 5.2 | 23.4 |
| | | ZSM-35 | 4.2 × 5.4 | 22.7 |
| | | ALPO-11 | 3.9 × 6.3 | 24.6 |
| 3 | 10 | ZSM-5 | 5.3 × 5.6 | 29.1 |
| | | ZSM-11 | 5.3 × 5.4 | 28.6 |
| | | Stilbite | 4.9 × 6.1 | 29.9 |
| | | ZSM-57 (10) | 5.1 × 5.8 | 29.6 |
| 4 | 12 | ZSM-12 | 5.5 × 5.9 | 32.4 |
| | | Mordenite | 6.5 × 7.0 | 45.5 |
| | | Beta (C-56) | 6.2 × 7.7 | 47.7 |
| | | Linde-L | 7.1 × 7.1 | 50.4 |
| | | Mazzite (ZSM-4) | 7.4 × 7.4 | 54.8 |
| | | ALPO$_4$-5 | 7.3 × 7.3 | 53.3 |

It can be seen that small pore, eight-ring zeolites have a Pore Size Index below about 17, the intermediate pore, 10-ring zeolites of about 22–30, and large pore, 12-ring zeolites above about 32. It is also apparent, that the 10-ring zeolites are grouped in two distinct classes; Type 2 with a Pore Size Index between about 22.7 and 24.6, and more broadly between about 20 and 26, and Type 3 with a Pore Size Index between 28.6 and 29.9, or more broadly, between about 28 and 31.

The zeolite useful for this invention are those of Type 2 with a Pore Size Index of 20–26.

Alternatively, these zeolites can be distinguished from Type 1 and Type 3 zeolites by their sorption characteristics. Equilibrium sorption data are listed in Table B below. While both Type 2 and Type 3 zeolites sorb more than about 40 mg n-hexane per gram zeolite, the Type 2 zeolites sorb less than 40 mg 3-methylpentane under the conditions specified, in contrast to Type 3 zeolites. Small pore, 8-ring zeolites sorb less than 15 mg of 3-methylpentane per gram of zeolite.

The equilibrium sorption are obtained most conveniently in a thermogravimetric balance by passing a stream of inert gas such as helium containing the hydrocarbon with the indicated partial pressure over the dried zeolite sample held at 90° C. for a time sufficient to obtain a constant weight.

This method of characterizing the Type 2 zeolites has the advantage that it can be applied to new zeolites whose crystal structure has not yet been determined. For mixtures of zeolites with amorphous material or for poorly crystallized samples, the numbers apply only to the crystalline portion.

Thus, zeolites useful for the present invention sorb 30 to 55 mg n-hexane and 15 to 40 mg 3-methylpentane per g dry zeolite in the hydrogen form.

TABLE B

| Equilibrium Sorption Data of Medium Pore Zeolites | | | |
|---|---|---|---|
| | | Amount sorbed, mg per g zeolite | |
| Type | Zeolite | n-Hexane[a] | 3-Methylpentane[b] |
| 2 | ZSM-22 | 40 | 20 |
| | ZSM-23 | 45 | 25 |
| | ZSM-35 | 50 | 25 |
| 3 | ZSM-5 | 103 | 61 |
| | ZSM-12 | 52 | 58 |
| | ZSM-57 | 60 | 70 |
| | MCM-22 | 89 | 79 |

[a] at 90° C., 83 torr n-hexane
[b] at 90° C., 90 torr 3-methylpentane

ZSM-22 is more particularly described in U.S. Pat. No. 4,556,477, the entire contents of which are incorporated herein by reference. ZSM-22 and its preparation in microcrystalline form using ethylpyridinium as directing agent are described in U.S. Pat. No. 4,481,177 to Valyocsik, the entire contents of which are incorporated herein by reference. For purposes of the present invention, ZSM-22 is considered to include its isotypes, e.g., Theta-1, Gallo-Theta-1, NU-10, ISI-1, and KZ-2.

ZSM-23 is more particularly described in U.S. Pat. No. 4,076,842, the entire contents of which are incorporated herein by reference. For purposes of the present invention, ZSM-23 is considered to include its isotypes, e.g., EU-13, ISI-4, and KZ-1.

ZSM-35 is more particularly described in U.S. Pat. No. 4,016,245, the entire contents of which are incorporated herein by reference. For purposes of the present invention, ZSM-35 is considered to include its isotypes, e.g., ferrierite, FU-9, ISI-6, NU-23, and Sr-D.

The zeolite catalyst used is preferably at least partly in the hydrogen form, e.g., HZSM-22, HZSM-23, or HZSM-35. Other metals or cations thereof, e.g. rare earth cations, may also be present. When the zeolites are prepared in the presence of organic cations, they may be quite inactive possibly because the intracrystalline free space is occupied by the organic cations from the forming solution. The zeolite may be activated by heating in an inert or oxidative atmosphere to remove the organic cations, e.g. by heating at over 500° C. for 1 hour or more. The hydrogen form can then be obtained by base exchange with ammonium salts followed by calcination, e.g. at 500° C. in air.

The catalysts employed in the present invention may also contain divalent or trivalent metal cations, preferably in amounts ranging from 0 to 3 wt %, more preferably from 0 to 2 wt %.

The metal may be incorporated into the catalyst by any suitable method such as impregnation or exchange onto the zeolite. The metal may be incorporated in the form of a cationic, anionic or a neutral complex, such as $Pt(NH_3)_4^{2+}$, and cationic complexes of this type are found convenient for exchanging metals onto a zeolite. Anionic complexes are also useful for impregnating metals into the zeolites.

Among the divalent metals suited to incorporation into the catalyst are those of Group IIA, e.g., Mg, Ca and Sr. Suitable trivalent metals include Fe, Al and the lanthanides. Included among the suitable divalent and trivalent metals are the Group VIIIA metals of which the noble metals such as Pd, Pt, Rh and Ru are believed particularly suited to use in the present invention. Among the foregoing metals are those which exhibit hydrogenation ability. Incorporation of hydrogenation metals is particularly useful in carrying out simultaneous butene isomerization and hydrogenation of dienes, e.g. butadiene, or alkynes such as acetylene.

It is generally desirable to incorporate the zeolite with another material resistant to the temperatures and other conditions employed in organic conversion processes. Such matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the zeolite, i.e., combined therewith, which is active, tends to improve the conversion and/or selectivity of the catalyst in certain organic conversion processes. However, for present purposes, inactive materials of low acidity such as silica or zirconia are preferred in that they prevent unwanted polymerization reactions engendered by more active materials such as alumina. Inactive materials can also suitably serve as diluents to control the amount of conversion in a given process so that products can be obtained economically and orderly without employing other means for controlling the rate of reaction.

Generally the catalyst of the present invention comprises 2 to 90 wt %, preferably 5 to 50 wt %, e.g., 10 to 30 wt %, of a suitable matrix material.

Frequently, zeolite materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the zeolite catalyst include the montmorillonite and kaolin family, which families include the sub-bentonites, and the kaolins commonly known as Dixie, McNamee, Georgia and Florida clays or others in which the main mineral constituents is halloysite, kaolinite, dickite, nacrite, or anauxite. Such clays can be used in the raw state as originally mined or initially subjected to calcination, acid treatment or chemical modification.

In addition to the foregoing materials, the zeolite can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

As noted above, of all the foregoing materials, silica is preferred as the matrix material owing to its relative inertness for catalytic polymerization reactions which are preferably minimized in the instant isomerization processes. The relative proportions of finely divided zeolite and inorganic oxide gel matrix vary widely with the zeolite content ranging from about 10 to about 98 percent by weight and more usually in the range of about 50 to about 95 percent by weight of the composite, say about 60 to 90 percent by weight of the composite.

The regeneration of spent zeolite catalyst used in the isomerization reaction is carried out oxidatively or hydrogenatively employing procedures known in the art. The catalyst of the present invention can be readily reactivated without significantly reducing selectivity for 2-olefins by exposing it to hydrogen for a suitable period, e.g., overnight, and temperature to effect reactivation. For example, the deactivated catalyst is heated in a flowing stream of hydrogen-containing gas to a temperature of 250° C. during 1 hour, and kept at 250° C. for 4 hours. Alternatively, the deactivated catalyst is heated to 350° C. in a flowing stream of inert gas such as nitrogen which contains 0.5% $O_2$ until the major exothermic temperature rise has subsided; the oxygen content is then increased stepwise to 1%, 3%, and finally to about 20%, and the temperature increased to 450° C. and held there for 6 hours.

Alpha value, or alpha number, of a zeolite is a measure of zeolite acidic functionality and is more fully described together with details of its measurement in U.S. Pat. No. 4,016,218, *J. Catalysis*, 6, pp. 278–287 (1966) and *J. Catalysis*, 61. pp. 390–396 (1980). The experimental conditions cited in the latter reference are used for characterizing the catalyst described herein. The zeolite catalyst of the present invention has an alpha value ranging from 2 to 300, preferably 5 to 200, based on the zeolite component, when composite catalysts are used.

Feedstream

Suitable organic feeds for the isomerization method of the present invention are those having an average carbon number of about 4 to 5. Such feeds contain 1-olefin, e.g. a $C_3$ to $C_5$ hydrocarbon stream comprising at least 2 wt % 1-olefin, e.g. at least 2 wt % 1-butene or at least 2 wt % 1-pentene. Such feedstocks can include a $C_4$ cut of a cracking process light gas. Such light gas can contain butene isomers in mixture with substantial amounts of paraffins including n-butane and isobutane and preferably contain less than 3 wt % isobutene. Such $C_4$ cuts can be obtained as the isobutylene-depleted $C_4$ effluent stream of an etherification unit wherein methanol and a catalytic cracking $C_4$ cut are reacted to form methyl tert-butyl ether which is separated from said effluent stream. Feeds containing minimal amounts of isobutylene are preferred inasmuch as isobutylene forms oligomerization by-products such as dimers more readily than linear olefins.

Mixtures containing cis-2-butene and trans-2-butene as well as 1-butene can be used. These mixtures can contain the linear butene isomers in a ratio that differs from the thermodynamic equilibrium ratio prevailing at the isomerization reaction temperature. The $C_4$ components usually contain a major amount of unsaturated compounds, such as 5–40% isobutylene, 20–55% linear butenes, and small amounts of butadiene.

The following table lists the thermodynamic linear butene isomer distribution from the thermodynamic data given in *The Chemical Thermodynamics of Organic Compounds*, D. R. Stull, E. F. Westrum, Jr., and G. C. Sinke, John Wiley & Sons, New York, 1969.

TABLE 1

| Temperature, °C. | Percent Composition | |
|---|---|---|
| | 1-Butene | 2-Butene |
| 25 | 2.6 | 97.4 |
| 100 | 6.0 | 94.0 |
| 200 | 10.4 | 89.6 |
| 300 | 15.4 | 84.6 |
| 400 | 20.1 | 79.9 |
| 500 | 24.3 | 75.7 |
| 600 | 28.0 | 72.0 |

The 1-butene-containing feed may also contain 2-butene, isobutylene, n-butane and/or isobutane, as well as $C_1$–$C_3$ and $C_5$+ hydrocarbons. In general, it is contemplated to use a stream comprising at least 10%, and preferably at least 20% butenes. Especially preferred feeds are the $C_4$ fractions obtained from catalytic cracking of higher boiling hydrocarbon fractions such as gas oil, as well as feeds obtained from coking of resid and from steam cracking of naphtha. Such feed can contain the four butene isomers as well as n-butane and isobutane. In one embodiment, the organic feedstock is a $C_4$ cut of a cracking process light gas and contains about 10 wt % 1-butene. Two typical compositions of commercial FCC $C_4$ cuts are set out in Table 2 below.

TABLE 2

| | Feed 1 Wt % | Feed 2 Wt % of | | |
|---|---|---|---|---|
| | Total | Total | Olefins | Linear Olefins |
| n-$C_4$ | 19.7 | 6.1 | — | — |
| i-$C_4$ | 46.0 | 29.3 | — | — |
| i-$C_4$= | 5.9 | 19.5 | 30.2 | — |
| 1-$C_4$= | 9.0 | 15.8 | 24.4 | 34.9 |
| 2-tr-$C_4$= | 11.2 | 17.1 | 26.5 | 38.0 |
| 2-cis-$C_4$= | 8.2 | 12.2 | 18.9 | 27.1 |
| | 100.0 | 100.0 | 100.0 | 100.0 |

In view of the desirability of carrying out the isomerization with a feed which comprises minimal isobutene, a preferred feed is the effluent of a liquid phase iso-olefin etherification reactor which employs alkanol and $C_4$ or $C_4$+ hydrocarbon feedstock, from which the alkyl tert-butyl ether product is separated out. Inasmuch as isobutene is reacted at nearly quantitative levels in this etherification, the effluent contains only small amounts of isobutene, e.g., less than 3 or even less than 1 wt % isobutene.

$C_4$+ heavier olefinic hydrocarbon streams may be used. Preferred is a $C_5$ cut containing 1-pentene, 2-pentene, isopentene, pentane and isopentane. Other suitable feedstocks include a $C_5$ cut of a cracking process light gasoline, e.g., one containing less than 6% isopentene. The $C_5$ cuts can be obtained as the isopentene-depleted $C_5$ effluent stream of an etherification unit wherein methanol and a catalytic cracking $C_5$ cut are reacted to form methyl tert-amyl ether which is separated from said effluent stream.

U.S. Pat. No. 4,605,787 to Chu et al., provides an example of etherification of isobutene with methanol. It can be carried out in the vapor phase at temperatures between 77° C. and 105° C. in contact with acidic ZSM-5 or ZSM-11 to produce MTBE in high conversion and selectivity. This patent is incorporated herein by reference as an example of suitable effluent which may be employed as feed to the method of the present invention.

The present invention provides a process for the selective dealumination of the zeolite used in double bond isomerization of terminal double bond olefins at the zeolite crystal surface by contacting the zeolite with a chelating agent capable of forming a chelate-Al complex. Suitable chelating agents include ethylenediamine tetraacetic acid (EDTA), nitrilotriacetic acid, acetylacetone (AcAc) and dicarboxylic acid. The treatment with chelating agent is believed to bind with aluminum from the crystal surface of the zeolite, rendering the aluminum inactive as an acid site and capable of removal from the zeolite by filtration and optionally with subsequent washing with a suitable solvent, e.g., water or organic solvents.

The invention therefore includes a process for the surface dealumination of the zeolite which comprises contacting with the chelating agent for a sufficient time to effect greater than about 20, 40 or even greater than 50% surface dealumination.

Prior to or following contact with chelating agent, the zeolite may be composited with a porous matrix material, such as alumina, silica, titania, zirconia, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia. The matrix may be in the form of a cogel. The relative proportions of zeolite component and inorganic oxide gel matrix may vary widely with the zeolite content ranging from between 1 to 99, more usually 5 to 80, percent by weight of the composite.

Suitable dicarboxylic acids for use in the process of this invention include oxalic, malonic, succinic, glutaric, adipic, tartaric, maleic, phthalic, or mixtures thereof. Oxalic acid is preferred. The dicarboxylic acid may be used in solution, such as an aqueous dicarboxylic acid solution. Tricarboxylic acids such as citric acid and higher polycarboxylic acids can also be used.

Generally, the acid solution has a concentration in the range from about 0.01 to about 4 M. Preferably, the acid solution concentration is in the range from about 1 to about 3 M.

The dicarboxylic acid is generally in a volume solution to volume catalyst ratio of at least about 1:1, preferably at least about 4:1.

Treatment time with the chelating agent is as long as required to provide the desired reduction in surface acidity. Generally the treatment time is at least about 10 minutes. Preferably, the treatment time is at least about 1 hour.

More than one chelating agent treatment step may be employed in the process of the present invention for enhanced deactivation of surface acidity.

The treatment temperature is generally in the range from about 32° F. to about reflux. Preferably, the treatment temperature is from about 15° C. to 93° C. (60° F. to 200° F.), and more preferably from 49° C. to 82° C. (120° F. to 180 F).

The dicarboxylic acid treatment of this invention may also be combined with other conventional dealumination techniques, such as steaming and chemical treatment.

In the examples which follow, the isomerization reactions were performed under pressure in the liquid phase in a fixed bed continuous flow reactor. A guard bed consisting of gamma alumina, reduced copper chromite (Oxy-Trap), and molecular sieve Zeolite 4A, was used to eliminate impurities from the $C_4$- mixture feed. The reaction products at various times on stream were analyzed by on-line gas chromatography. Temperatures and flow rates, expressed as WHSV=g feed per g zeolite per hour, are indicated in the tables.

EXAMPLE 1 (Comparative)

This example is illustrative of the double bond isomerization with an unmodified (non-surface acidity deactivated) ZSM-23/SiO$_2$ catalyst. This catalyst was prepared as follows:

157 parts distilled water were charged to an autoclave, followed by 2.33 parts NaOH solution (50% by weight), 1.0 part aluminum sulfate (17.2% Al$_2$O$_3$), and 1.0 part ZSM-23 seeds (100% basis). After mixing thoroughly, 26.4 parts of precipitated silica (HiSil 233 TM) and then 9.33 parts of pyrrolidine were added and mixed thoroughly. The autoclave was heated to 160° C. with stirring and maintained at these conditions until crystallization was complete. The product was identified as ZSM-23 by X-ray diffraction. After flashing the pyrrolidine, the slurry was cooled, filtered, washed, and dried at 120° C. The catalyst was then exchanged with 1 N ammonium nitrate solution (5ml per gram of catalyst) three times at room temperature for 3 hours. The catalyst was rinsed with deionized/distilled water, dried under flowing air at room temperature, and calcined in nitrogen at 538° C. until all the ammonium was removed.

65 parts of the resulting ZSM-23 product were combined with 20 parts of precipitated silica (Ultrasil VN3SP, 100% solids basis) and 15% colloidal silica (Ludox HS-30). Deionized water was added to give an extrudable mull and the mix extruded to 1/16 inch cylindrical extrudate. The extrudate was dried at 121° C., calcined in nitrogen at 538° C. for 2 hours, and then in air for 3 hours. The extrudate was then exchanged with 1N ammonium nitrate solution (5 ml per gram of catalyst) at room temperature for 1 hour. The exchange was repeated 3 times, the extrudate was rinsed with deionized water, dried at 121° C., and calcined in air at 538° C. for 3 hours. The catalyst was then steamed at 398 C for 24 hours.

The resulting product, in the form of 14–30 mesh particles, was placed into an electrically heated stainless steel tubular reactor. A simulated alkylation feed from a methyl tert-butyl ether (MTBE) unit containing small amounts of isobutylene having the composition set out in Table 3 was pumped through the reactor in a down-flow mode. The product distribution and operating conditions are set out in Table 4 below.

TABLE 3

| Feed Composition | | |
|---|---|---|
| Component | Total | Olefins |
| i-C$_4$° | 47.8 | |
| n-C$_4$=° | 20.8 | |
| i-C$_4$= | 0.4 | 1.3 |
| 1-C$_4$= | 10.0 | 31.8 |
| 2-C$_4$ | 21.0 | 66.9 |

TABLE 4

| Product Distribution Obtained Over Unmodified ZSM-23/SiO$_2$ | | | | | |
|---|---|---|---|---|---|
| Operating Conditions | | Olefinic Product Distribution (wt %) | | | |
| T (°C.) | WHSV | 1-C$_4$= | 2-C$_4$= | i-C$_4$= | C$_8$=+ |
| 80 | 6.1 | 5.0 | 90.6 | 0 | 4.4 |

TABLE 4-continued

| Product Distribution Obtained Over Unmodified ZSM-23/SiO$_2$ | | | | | |
|---|---|---|---|---|---|
| Operating Conditions | | Olefinic Product Distribution (wt %) | | | |
| T (°C.) | WHSV | 1-C$_4$= | 2-C$_4$= | i-C$_4$= | C$_8$=+ |
| 60 | 2.1 | 6.2 | 89.7 | 0.0 | 4.1 |

EXAMPLE 2

(Comparative)

A base-selectivated catalyst was prepared by treating 343 parts of catalyst of Example 1 with 1 part of 2,4,6-collidine dissolved in pentane. The resulting slurry was thoroughly stirred and heated at about 50° C. until dryness. The resulting catalyst was used in a double bond isomerization process using a feed similar to that of Example 1. The composition of the feed is set out below in Table 5. The product distribution and operating conditions are set out in Table 6 below. Comparison of the product distributions of the double bond isomerization products of Examples 1 and 2 indicates that the base-selectivation treatment of the ZSM-23/SiO$_2$ catalyst is somewhat effective in reducing the undesired formation of oligomers (C$_8$+) Example 1 shows that on the unmodified ZSM-23/SiO$_2$ catalyst, all the isobutylene reacted to produce oligomers, while on the collidine modified ZSM-23/SiO$_2$ catalyst of Example 2, only 28% of the isobutylene was consumed, with a corresponding reduction in the amount of undesirable oligomer formed.

TABLE 5

| Feed Composition | | |
|---|---|---|
| Component | Total | Olefins |
| i-C$_4$° | 44.1 | |
| n-C$_4$=° | 24.2 | |
| i-C$_4$= | 0.57 | 1.8 |
| 1-C$_4$= | 8.5 | 26.8 |
| 2-C$_4$ | 22.7 | 71.4 |

TABLE 6

| Product Distribution Obtained Over Base-Selectivated ZSM-23/SiO$_2$ | | | | | |
|---|---|---|---|---|---|
| Operating Conditions | | Olefinic Product Distribution (wt %) | | | |
| T (°C.) | WHSV | 1-C$_4$= | 2-C$_4$= | i-C$_4$= | C$_8$=+ |
| 95 | 1.4 | 6.2 | 90.1 | 1.3 | 2.3 |

EXAMPLE 3

A selectivated catalyst in accordance with the present invention was prepared by treating 1 part of the ZSM-23/SiO$_2$ catalyst of Example 1 with 30 parts of an aqueous 2M oxalic acid solution at 77° C. (170° F.) for three hours, then cooled down to ambient temperature, filtered and washed with water to remove excess oxalic acid. The resulting catalyst was used in a double bond isomerization process using the 1-butene containing feed of Table 5 above. The product distribution and operating conditions are set out in Table 7 below. Comparison of the product distributions of the double bond isomerization products of Examples 1 and 3 indicates that the dealumination-selectivation treatment of the ZSM-23/SiO$_2$ catalyst is effective in reducing the undesired formation of oligomers (C$_8$+) Example 1 shows that on the unmodified ZSM-23/SiO$_2$ catalyst, all the isobutylene reacted to produce oligomers, while on the oxalic acid-modified ZSM-23/SiO$_2$ catalyst of Example 3, a significantly lower amount of oligomer was produced (4.4 wt % vs. 2.6 wt %). Although slightly higher amounts of oligomer were produced as compared to the base-selectivated catalyst of Example 2, The isomerization activity of the catalyst of the present invention was significantly greater, allowing operation at increased space velocity (1.8 vs. 1.4) and reduced temperature (80° C. vs. 95° C.). Operation at lower temperature contributes to enhanced internal double bond selectivity.

TABLE 7

Product Distribution Obtained Over Oxalic Acid Treated ZSM-23/SiO$_2$

| Operating Conditions | | Olefinic Product Distribution (wt %) | | | |
|---|---|---|---|---|---|
| T (°C.) | WHSV | 1-C$_4$= | 2-C$_4$= | i-C$_4$= | C$_8$=+ |
| 80 | 1.8 | 5.0 | 92.3 | * | 2.6 |

*not analyzed

It Is Claimed:

1. A method for double bond isomerization of terminal double bond olefin-containing feedstock which comprises contacting said feedstock under double bond isomerization conditions at temperatures of 20° to 150° C. with a double bond isomerization catalyst comprising a zeolite capable of sorbing 30 to 55 mg n-hexane at 90° C., 83 torr, and 15 to 40 mg 3-methylpentane at 90° C., 90 torr, per g dry zeolite in the hydrogen form; whose surface has been at least partially deactivated for acid catalyzed reactions by treatment with a chelating agent capable of forming a chelate-Al complex, said chelating agent possessing an average cross section diameter greater than that of the zeolite pores.

2. The method of claim 1 wherein said isomerizing is carried out at weight hourly space velocities of the feedstock (based on total feed) between 0.5 and 100 hr$^{-1}$, and total pressure between 100 and 10000 kPa.

3. The method of claim 1 wherein said isomerizing is carried out in the liquid phase at weight hourly space velocities of the feedstock (based on total feed) between 1 and 80 hr$^{-1}$; and total pressure between 300 and 6000 kPa.

4. The method of claim 1 wherein said isomerizing is carried out in the liquid phase.

5. The method of claim 1 wherein said zeolite has the framework structure of a zeolite selected from the group consisting of ZSM-22, ZSM-23, and ZSM-35.

6. The method of claim 1 wherein said zeolite has the structure of ZSM-22.

7. The method of claim 1 wherein said zeolite has the structure of ZSM-23.

8. The method of claim 1 wherein said zeolite has the structure of ZSM-35.

9. The method of claim 1 wherein said catalyst comprises 2 to 90 wt % of a matrix selected from the group consisting of silica, alumina, and silica-alumina.

10. The method of claim 1 wherein said catalyst comprises 5 to 50 wt % of a silica matrix.

11. The method of claim 1 wherein said chelating agent is selected from the group consisting of EDTA, nitrilotriacetic acid, acetylacetone, dicarboxylic acid, and tricarboxylic acid.

12. The method of claim 11 wherein said chelating agent comprises aqueous dicarboxylic acid solution.

13. The method of claim 12 wherein said dicarboxylic acid is in a concentration in the range of from about 0.01 to about 4 M.

14. The method of claim 11 wherein said dicarboxylic acid is selected from the group consisting of oxalic, malonic, succinic, glutaric, adipic, maleic, phthalic, tartaric and mixtures thereof.

15. The method of claim 12 wherein said dicarboxylic acid is oxalic acid.

16. The method of claim 1 wherein said feedstock comprises C$_4$ to C$_{12}$ olefins.

17. The method of claim 1 wherein said feedstock is a C$_3$ to C$_5$ hydrocarbon stream comprising at least 10 wt % 1-butene.

18. The method of claim 1 wherein said feedstock is a C$_4$-cut of a cracking process light gas.

19. A method for conversion of terminal double bond olefin to internal double bond olefin which comprises contacting a terminal double bond olefin-containing organic feedstock with a catalyst comprising a zeolite having a Pore Size Index of 20 to 26, under double bond isomerization conditions at temperatures of 20° to 150° C., said zeolite having been contacted with dicarboxy acid under conditions sufficient to form a chelate-Al complex with aluminum atoms on the zeolite surface.

20. The method of claim 19 wherein said dicarboxylic acid is oxalic acid and said terminal double bond olefin is 1-butene.

* * * * *

UNITED STATES PATENT AND TRADEMARK OFFICE
CERTIFICATE OF CORRECTION

PATENT NO. : 5,304,695
DATED : April 19, 1994
INVENTOR(S) : Werner O. Haag et al It is certified that error appears in the above-indentified patent and that said Letters Patent is hereby corrected as shown below:

Col. 14, line 43 (claim 19), "dicarboxy" should read --dicarboxylic.--

Signed and Sealed this

Twenty-sixth Day of July, 1994

Attest:

BRUCE LEHMAN

Attesting Officer   Commissioner of Patents and Trademarks